United States Patent [19]

Chase

[11] Patent Number: 4,642,257

[45] Date of Patent: Feb. 10, 1987

[54] MAGNETIC OCCLUDING DEVICE

[76] Inventor: Michael Chase, 6001 Amos Ave., Lakewood, Calif. 90712

[21] Appl. No.: 744,258

[22] Filed: Jun. 13, 1985

[51] Int. Cl.[4] .......................... A61N 1/42; B32B 35/00

[52] U.S. Cl. .......................................... 428/63; 156/94; 428/900

[58] Field of Search ....................... 428/63, 542.2, 900; 156/94

[56] References Cited

U.S. PATENT DOCUMENTS

| | | | |
|---|---|---|---|
| 1,395,982 | 11/1921 | Gee | 40/621 |
| 2,177,905 | 10/1939 | McKeehan | 40/621 X |
| 2,507,559 | 5/1950 | D'Andrea | 248/206.5 X |
| 2,557,398 | 6/1951 | Teetor | 40/10 R |
| 2,557,399 | 6/1951 | Teetor | 40/621 X |
| 2,634,444 | 4/1953 | Coleman | 15/121 |
| 2,693,654 | 11/1954 | Clark | 40/1.5 |
| 3,164,352 | 1/1965 | Weaver | 248/214 |
| 3,176,364 | 4/1965 | Dritz | 24/304 |
| 3,296,645 | 1/1967 | Shore | 15/220 A |
| 3,416,195 | 12/1968 | Borthwick | 428/900 X |
| 3,460,303 | 8/1969 | Algrain et al. | 428/38 X |
| 3,518,884 | 7/1970 | Wood, Jr. | 248/206.5 X |
| 3,654,711 | 4/1972 | Taylor | 428/900 X |
| 3,670,435 | 6/1972 | Steward | 40/621 X |
| 3,922,747 | 12/1975 | Kaftan | 428/900 X |
| 4,163,817 | 8/1979 | DiCarlantonio et al. | 428/63 X |
| 4,222,162 | 9/1980 | Levy et al. | 428/63 X |
| 4,236,331 | 12/1980 | Mattson | 40/621 X |
| 4,242,823 | 1/1981 | Bruno | 40/621 |
| 4,549,532 | 10/1985 | Baermann | 428/900 X |

FOREIGN PATENT DOCUMENTS

| | | | |
|---|---|---|---|
| 497373 | 5/1929 | Fed. Rep. of Germany | 428/900 X |

*Primary Examiner*—Henry F. Epstein

*Attorney, Agent, or Firm*—Knobbe, Martens, Olson & Bear

[57] ABSTRACT

A decorative magnetic occluding device for decoratively and uniformly occluding opposing surface portions of a non-magnetic panel which includes a matched pair of sheet magnets, each being the mirror image configuration of the other. Each magnet has a decorative surface, which is a mirror image configuration of the decorative surface of the other magnet, and an opposite magnetized surface. The magnetized surfaces have alternating North and South stripes of polarity, with the stripes of polarity of one of the magnetized surfaces being offset by one stripe from the corresponding stripes of polarity of the other of the magnetized surfaces. Each magnet has visual orientation means to ensure that the corresponding stripes of polarity of each magnet will be opposite in polarity when the magnets are mated.

13 Claims, 4 Drawing Figures

MAGNETIC OCCLUDING DEVICE

FIELD OF THE INVENTION

The present invention relates to a magnetic occluding device, and, more particularly, to a decorative magnetic occluding device for decoratively and uniformly occluding opposing surface portions of a non-magnetic panel, such as a fabric screen door closure.

BACKGROUND OF THE INVENTION

The hazards of a person accidentally walking into a glass door, a floor-to-ceiling glass window or the like are well known. Although the most common result is moderate pain from the impact, coupled with shock and embarrassment, the impact pain can be severe, and, in some cases the glass can even break causing fatal or near fatal injury. Accordingly, the use of warning signs or markers on these glass panels has become widespread, and, in some cases, required by law. Most commonly, these signs or markers are permanently affixed to the surface of the glass, e.g., by painting, use of adhesive decals or the like. Although these conventional signs and markers adequately perform their safety function, they cannot be easily removed, relocated or replaced. Further, they are generally unsightly from the opposite side of the glass, which is typically open to viewing. While a corresponding sign or marker can be affixed in a corresponding location on the opposite side of the glass, precision alignment is difficult and the replacement, relocation and removal difficulties are doubled.

Although some products have been developed which minimize the removal, replacement and relocation difficulties, none has been entirely satisfactory. For example, one such product consists of a thin plastic decal which relies on the affinity of the material to cling to smooth glass, in the nature of modern plastic food wrap materials, rather than utilizing a glue adhesive. However, the adhesion is weak and diminishes with time. Use of these decals on both sides of the glass still requires difficult precision alignment. Finally, these decals will not adhere to most panels other than smooth glass, such as many plastics, textured glass and screens.

Another method of attaching a sign to a window so that it is easily removable is disclosed in German Pat. No. 497,373, wherein the sign is made of a magnetizable material, which is held in place by means of a magnet on the opposite side of the window. This device suffers from the disadvantage that the magnet is unsightly from the opposite side of the window. Further, with larger gaps between the magnet and the sign or with heavier signs, a bulkier and heavier magnet is required which adds to the unsightliness, as well as the exposure to accidental displacement by bumping, wind, rain, or the like. In the case of modern fabric screens, a metal sign and a heavy magnet can cause permanent stretching and distortion of the screen material.

Accordingly, there remains a need for a device for mounting signs or markers to a variety of panels, such as smooth and textured glass, various plastics and fabric screens, which is easily mounted, removed, replaced and relocated, which has strong adhesive properties and which is lightweight and attractive from both sides of the panel.

SUMMARY OF THE INVENTION

According to the present invention, there is provided a decorative magnetic occluding device for decoratively and uniformly occluding opposing surface portions of a non-magnetic panel. The unique device is particularly suitable for mounting signs or markers, such as safety warnings, to a wide variety of panels, such as smooth and textured glass, various plastics and fabric screens. The device is easily mounted, removed, replaced and relocated. It has strong adhesive properties, while being lightweight and attractive from both sides of the panel. In addition to mounting signs, including safety markers for preventing unintentional contact with a transparent or semi-transparent closure panel, such as a glass or screen door, the device can be used for easily and removably covering imperfections in non-magnetic panels, such as attractively patching a hole in a fabric screen door.

The magnetic occluding device of the present invention includes a matched pair of sheet magnets, each being the mirror image configuration of the other. Each magnet has a decorative surface, which is a mirror image configuration of the decorative surface of the other magnet. The opposite surface of each magnet is the magnetized surface. The magnetized surfaces have alternating North and South stripes of polarity, with the stripes of polarity of one of the magnetized surfaces being offset by one stripe from the corresponding stripes of polarity of the other of the magnetized surfaces, so that when the magnets are mated, each stripe of polarity of each magnet will oppose a stripe of opposite polarity on the other magnet.

In order to ensure that the corresponding stripes of polarity of each magnet will be opposite when the magnets are mated, each magnet has a visual orientation means. The visual orientation means can include indicia, such as words or pictures, or it can be accomplished by simply providing the magnets with mirror image asymmetric configurations, so that when the magnets are mated with their configurations aligned, the proper alternating polarity is achieved.

In the especially preferred embodiment, the sheet magnets are flexible and are particularly suitable for use on thin flexible panels, such as fabric screen door closures, which tend to flex when exposed to bumps, high winds and the like.

DESCRIPTION OF THE PREFERRED EMBODIMENT

Figure 1:
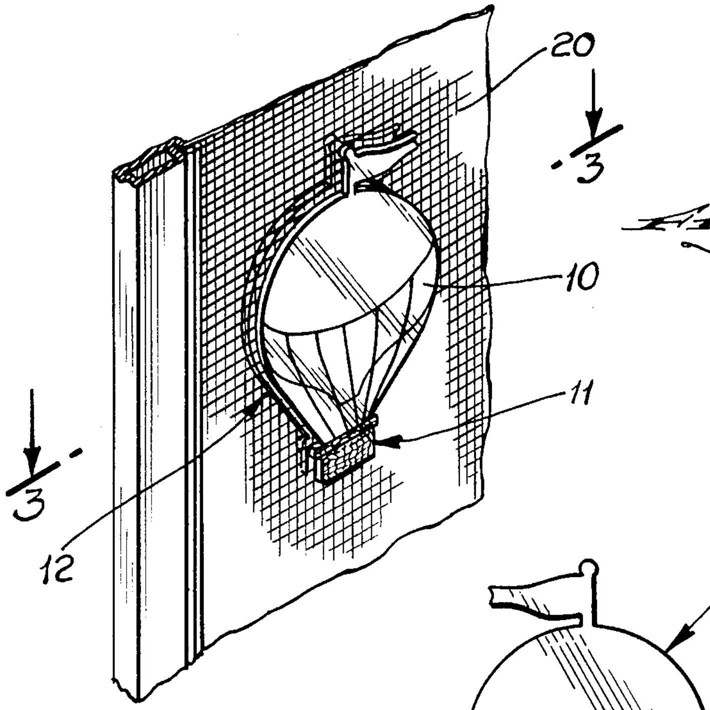
FIG. 1 is a perspective view of the magnetic occluding device of the present invention mounted on a portion of a screen door.
Figure 2:
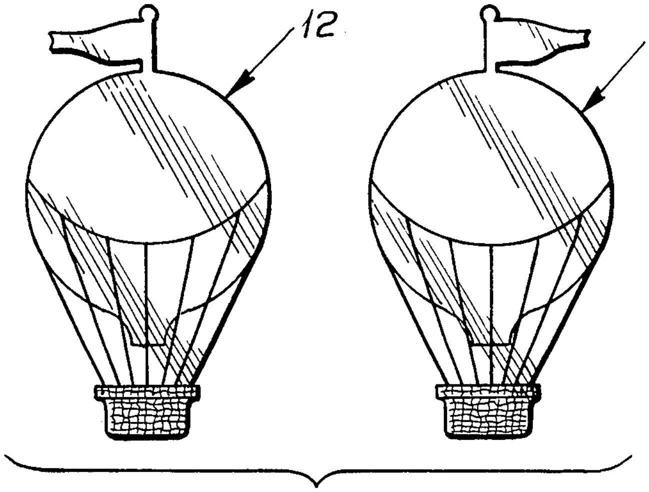
FIG. 2 is a front elevational view of the two sheet magnets of the device of FIG. 1 shown side by side with the decorative surfaces exposed.

Referring to the drawings in greater detail, FIG. 1 is a perspective view showing an embodiment of the magnetic occluding device 10 mounted on a portion of a screen door closure 20. Magnetic occluding device 10 includes a matched pair of sheet magnets 11 and 12. As best shown in FIG. 2, which shows sheet magnets 11 and 12 side by side with their decorative surfaces exposed, each is the mirror image configuration of the other. Accordingly, when the magnets are mounted, as in FIG. 1, there is complete uniform alignment so that occluding device 10 appears as a unitary structure, which is attractive from both sides of screen closure 20.

Figure 3:
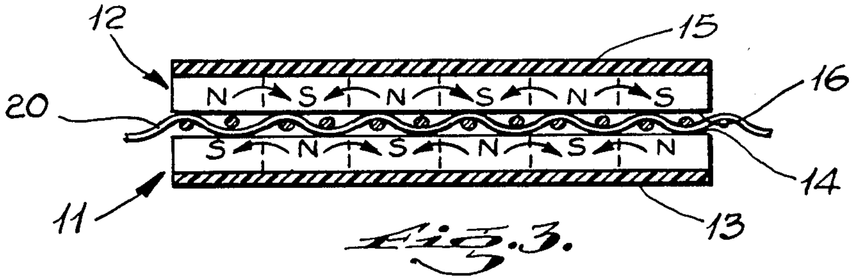
FIG. 3 is a cross-sectional view of the device of FIG. 1 taken along the lines III—III of FIG. 1.

In order to achieve complete uniform alignment when magnets 11 and 12 are mounted on opposing surfaces of a panel, not only must they have mirror image configurations, they must also have complementing magnetic properties to insure aligned magnetic adhesion. As shown in FIG. 3, which is a cross-section of occluding device 10 of FIG. 1, taken along the line III—III of FIG. 1, sheet magnet 11 has a decorative surface 13 and an opposite magnetic surface 14. Similarly, sheet magnet 12 has a decorative surface 15 and an opposite magnetic surface 16. Each of the magnetized surfaces has alternating North and South stripes of polarity, with the stripes of polarity of magnet 11 being offset by one stripe from the corresponding stripes of polarity of magnet 12. Thus, when the sheet magnets are mounted on opposing surfaces of a panel, each stripe of polarity of one magnet will always be opposing a stripe of opposite polarity so that optimum magnetic adhesion is achieved with sheet magnets 11 and 12 uniformly aligned with respect to each other. Although vertical stripes of polarity are shown in this embodiment, stripes of polarity can vary in radial orientation, as long as the orientation is complimentary as between the two sheet magnets. Furthermore, the use of sheet magnets with a plurality of stripes of polarity, as opposed to single pole magnets, maximizes the adhesion and uniformity characteristics of the device when mounted on a panel.

In the embodiment which is especially preferred, the sheet magnets are flexible, which makes them particularly suitable for use on flexible panels such as fabric screens. Flexible magnets are less apt to be dislodged when a screen door is bumped or exposed to high wind and the like. Such flexible sheet magnets are commercially available, such as for example from B.F. Goodrich Company of Akron, Ohio and Magnet Sales and Manufacturing Company of Culver City, Calif. and typically comprise a composite material, including a ferromagnetic material held in place by a thermoplastic binder. In the manufacture of these flexible sheet magnets, ferromagnetic material, such as barium ferrite, is embedded in the thermoplastic binder, and then the composite is exposed to a strong electromagnetic field having alternating North and South poles, which causes the ferromagnetic material in the sheet to align itself in alternating North and South poles.

Figure 4:
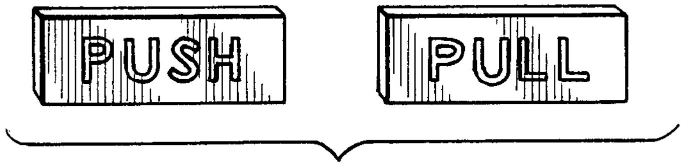
FIG. 4 is a perspective view of another matched pair of sheet magnets of a device in accordance with the present invention shown side by side with their decorative surfaces exposed.

A final requirement of the magnetic occluding device of the present invention is that each magnet must have a visual orientation means for ensuring that the corresponding stripes of polarity of each of the magnetized surfaces will be opposite when the magnets are mated on opposing surface portions of a panel with their decorative surfaces exposed. Otherwise, misalignment would result. In the case where the magnets have asymmetrical configurations, such as magnets 11 and 12 in FIG. 2, the asymmetry provides the requisite visual orientation so that proper mating is ensured. Otherwise, indicia, such as words or pictures, are provided on each of the magnets to ensure alignment. For example, as shown in FIG. 4, the magnets have a rectangular configuration and letter indicia on the decorative surfaces of each magnet. In this case, the words PUSH and PULL, will insure proper alignment, as long as each of the words is exposed and readably right side up when the magnets are mated. In the case of totally symmetrical magnets with totally symmetrical decorative surfaces, such as a circular plain colored surface, the orientation indicia can be located on the edges or on the hidden magnetized surfaces of the magnets.

Thus, the decorative magnetic occluding device of the present invention is easy to mount with a completely uniform configuration so as to appear as a unitary structure, attractive from both sides of the panel. The device is easily removed, with no unsightly residue left behind, and can be conveniently replaced or relocated. The magnetic adhesion is strong and uniform, and the device can be used with a wide variety of panels, such as smooth and textured glass, plastic and fabric screens. The device can be used purely for decoration, for occluding a portion of a transparent or semi-transparent panel as a safety warning, for attractively and easily covering imperfections in a panel, such as a hole in a screen, and the like. The device is lightweight and attractive from both sides. When used with thin panels, such as fabric screen door closures, flexible sheet magnets as thin as about 0.030 inch, weighing only approximately 0.280 pounds per cubic inch, can be used satisfactorily. These thin and lightweight flexible sheet magnets thus do not add significant weight to the panel and will not cause stretching or sagging when used on a thin fabric screen. Because of the thinness of the the magnets, exposure to displacement forces such as bumping, wind, rain and the like is minimized. The thinness of the magnets eliminates unattractive bulkiness when viewed from the side and renders the magnets especially suitable for use on adjacent sliding panels where the clearance between the panels is minimal.

While the preferred embodiments of the present invention have been described and illustrated, it will be obvious to those skilled in the art that various changes and modifications can be made without departing from the spirit of the present invention. For example, while two representative designs of the occluding device have been described and illustrated, the shapes, sizes, configurations, and decorative indicia which may be used are unlimited. Accordingly, the scope of the present invention is deemed to be limited only by the following claims.

What is claimed is:

1. A decorative magnetic occluding device for decoratively and uniformly occluding opposing surface portions of a non-magnetic panel comprising a matched pair of sheet magnets;

each being the mirror image configuration of the other;

each magnet having a decorative surface, which is a mirror image configuration of the decorative surface of the other magnet, and an opposite magnetized surface, said magnetized surfaces having alternating North and South stripes of polarity, the stripes of polarity of one of said magnetized surfaces being offset by one stripe from the corresponding stripes of polarity of the other of said magnetized surfaces; and each magnet having visual orientation means for insuring that the corresponding stripes of polarity of said magnetized surfaces will be opposite in polarity when said magnets are mated on opposing surface portions of a non-magnetic panel with the decorative surfaces exposed.

2. The magnetic device according to claim 1 wherein the configuration of said magnets is asymmetrical and wherein the asymmetry provides said visual orientation means.

3. The magnetic device according to claim 1 wherein said visual orientation means comprises indicia on each of said magnets.

4. The magnetic device according to claim 1 wherein said magnets are flexible.

5. The magnetic device according to claim 4 wherein said non-magnetic panel is a fabric closure screen.

6. A method for preventing unintentional contact with either side of a two-sided non-magnetic closure panel comprising the steps of placing one of said matched pair of sheet magnets of claim 1 on one of said sides of said panel followed by placing the other of said matched pair of sheet magnets on the other of said sides of said panel opposing the first placed sheet magnet so that said sheet magnets are in mating engagement with their decorative surfaces aligned and exposed.

7. The method according to claim 6 wherein said panel is a fabric screen.

8. The method according to claim 6 wherein said panel is glass.

9. The method according to claim 6 wherein said panel is plastic.

10. The method according to claim 6 wherein said panel is transparent.

11. A method for removably covering an imperfection in a two-sided non-magnetic panel comprising the steps of placing one of said matched pair of sheet magnets of claim 1 on one side of said panel at the location of said imperfectiion followed by placing the other of said matched pair of sheet magnets on the other side of said panel opposing the first placed sheet magnet so that said sheet magnets are in mating engagement with their decorative surfaces aligned and exposed and so that the imperfection is occluded by said sheet magnets.

12. A method for patching a hole in a two-sided non-magnetic panel comprising the steps of placing one of said matched pair of sheet magnets of claim 1 on one side of said panel at the location of said hole followed by placing the other of said matched pair of sheet magnets on the other side of said panel opposing the first placed sheet magnet so that said sheet magnets are in mating engagement with their decorative surfaces aligned and exposed and so that the hole is occluded by said sheet magnets.

13. A method for removably mounting a sign on a two-sided non-magnetic panel so as to be readable from both sides of said panel comprising the steps of placing one of said matched pair of sheet magnets of claim 1 on one side of said panel followed by placing the other of said matched pair of sheet magnets on the other side of said panel opposing the first placed sheet magnet so that said sheet magnets are in mating engagement, wherein the decorative surfaces of said sheet magnets bear the desired sign indicia.

* * * * *